US00PP24223P3

(12) United States Plant Patent
Olesen

(10) Patent No.: US PP24,223 P3
(45) Date of Patent: Feb. 11, 2014

(54) ***ROSA* HYBRID VARIETY DENOMINATION 'POULNAP003'**

(50) Latin Name: ***Rosa* hybrid**
Varietal Denomination: Poulnap003

(75) Inventor: Mogens Nyegaard Olesen, Fredensborg (DK)

(73) Assignee: Roser A/S, Fredensborg (DK)

( * ) Notice: Subject to any disclaimer, the term of this patent is extended or adjusted under 35 U.S.C. 154(b) by 61 days.

(21) Appl. No.: 13/507,021

(22) Filed: May 31, 2012

(65) Prior Publication Data

US 2013/0326760 P1 Dec. 5, 2013

(51) Int. Cl.
*A01H 5/00* (2006.01)

(52) U.S. Cl.
USPC ..... Plt./145

(58) Field of Classification Search
USPC ..... Plt./145
See application file for complete search history.

*Primary Examiner* — Annette Para

(57) ABSTRACT

A new garden rose plant of the Floribunda class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulnap003'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2002 and the resulting seeds were planted in a controlled environment in Fredensborg, Denmark. The new variety, named 'Poulnap003', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulnap003' from all other varieties of which we are aware.

As part of the rose development program, Mogens N. Olesen germinated the seeds from the aforementioned hybridization during winter of 2002 and conducted evaluations on the resulting seedlings in a controlled environment in Fredensborg, Denmark. 'Poulnap003' was selected in the spring of 2003 by the inventor as a single plant from the progeny of the aforementioned hybridization.

Asexual reproduction of 'Poulnap003' by traditional budding and rooted cuttings was first done by Mogens N. Olesen in the nursery in Fredensborg, Denmark in July, 2003. This initial and other subsequent asexual propagations conducted in controlled environments have demonstrated that the characteristics of 'Poulnap003' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulnap003'. Specifically illustrated in the drawings are flowers at various stages of development, flower in parts, leaves, and stems.

DETAILED DESCRIPTION OF THE VARIETY

Figure 1:
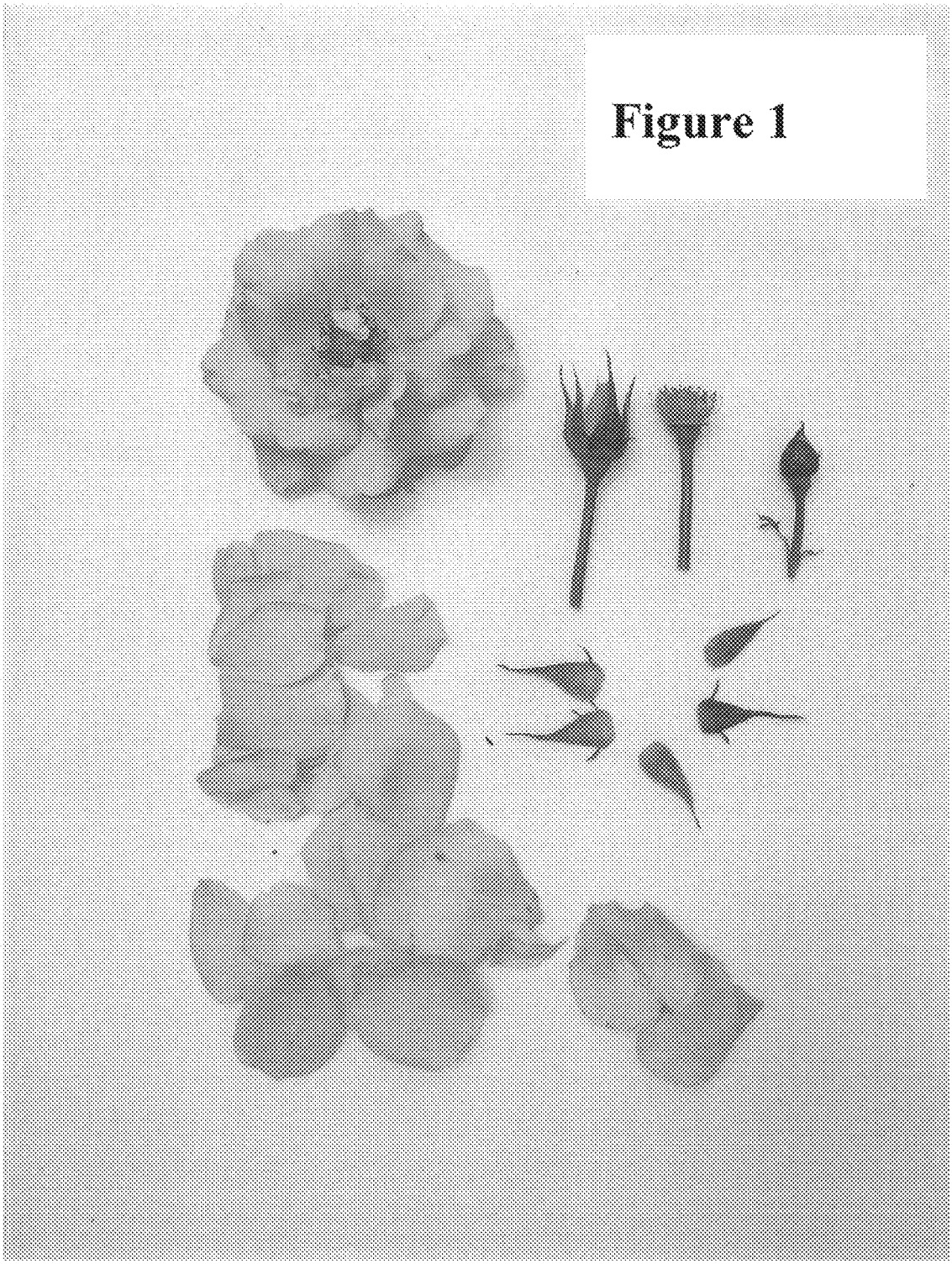
Figure 2:
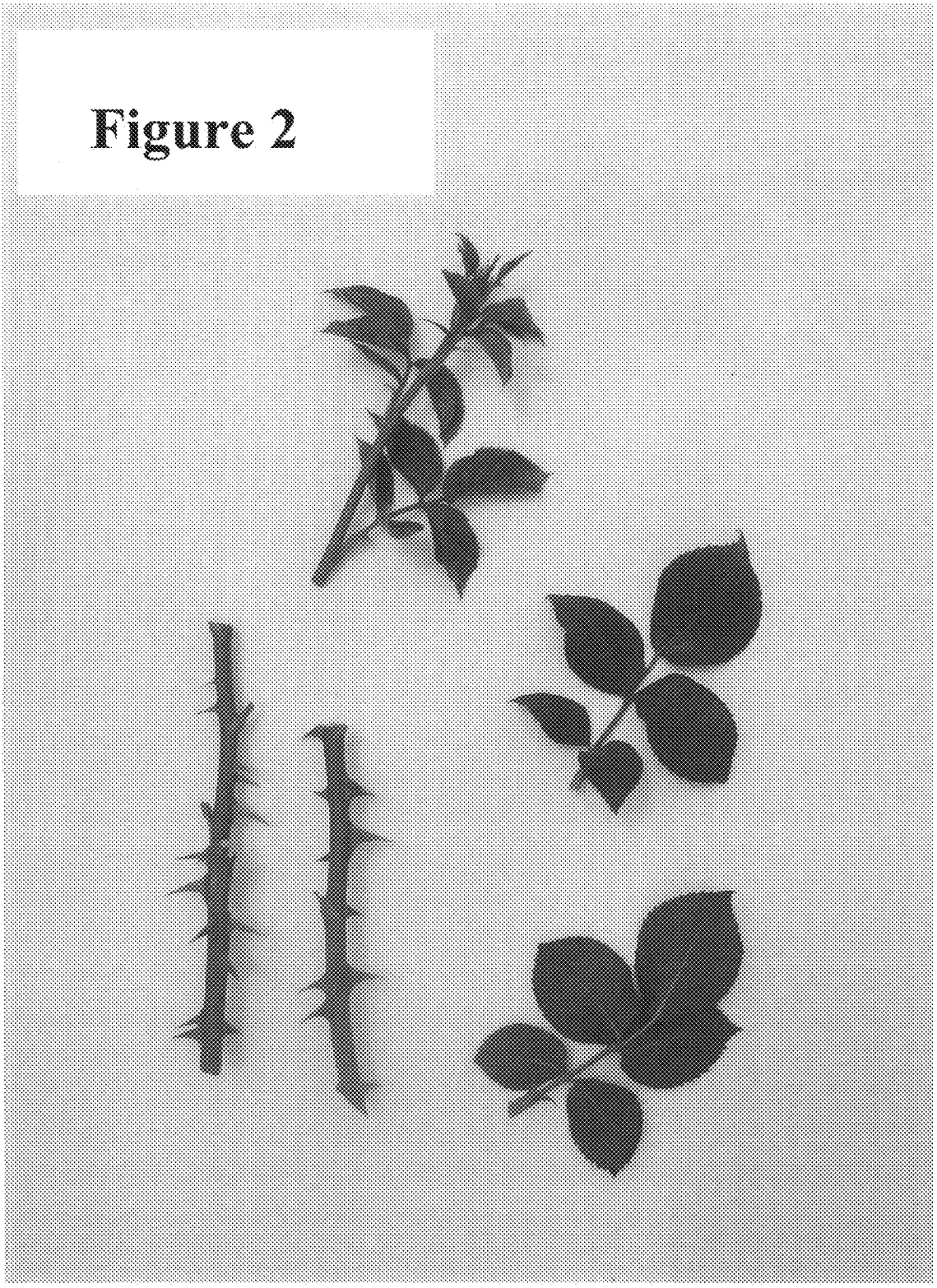

The following is a description of 'Poulnap003', as observed in its growth in in a field nursery in Bakersfield, Calif. 2 years of age, and were grown on their own roots. Color references are made using The Royal Horticultural Society (London, England) Colour Chart, 2001, except where common terms of color are used.

For a comparison, several physical characteristics of the rose variety 'Poulreb', U.S. Plant Pat. No. 12,534 are compared to 'Poulnap003' in Chart 1.

CHART 1

| | 'Poulnap003' | 'Poulreb' |
|---|---|---|
| Petal Count | 33 | 60 to 75 |
| Flower Diameter | 100 mm | 70-80 mm |
| General Tonality of Flower Color | Yellow-Green Group 12B | Yellow Group 8B |

FLOWER AND FLOWER BUD

Blooming habit: Continuous.
Flower bud:

*Size*.—Upon opening, 22 mm in length from base of receptacle to end of bud. Bud diameter is 14 mm.

*Bud form*.—Urceolate.

*Bud color*.—As sepals divide petals are Yellow Group 13A with intonations of Orange Group 28B.

*Sepal inner surface*.—Color: Yellow-Green Group 144C with intonations of Greyed-Orange Group 176A. Surface: Smooth. Weak pubescence.

*Sepal outer surface*.—Color: Yellow-Green Group 144A with intonations of Greyed-Orange Group 176A. Texture: Somewhat rough.

*Sepal shape*.—Apex: Cirrhose. Base: Flat at union with receptacle.

*Sepal margin*.—Margins have weak foliaceous appendages on three of the five sepals.

*Sepal size*.—35 mm long by 13 mm wide.

*Receptacle*.—Texture: Smooth. Size: 7 mm in height by 8 mm wide. Color: Yellow-Green Group 144A. Shape: Urn shaped.

*Pedicel*.—Surface: Smooth. Length: 25 to 50 mm. Diameter: 2 to 3 mm. Color: Yellow-Green Group 144A with moderate anthocyanic pigments the color of Greyed-Red Group 178A. Strength: Strong.

*Peduncle*.—Length: 30 to 40 cm. Diameter: 4 mm. Color: Yellow-Green Group 144A. Texture: Smooth.

*Flower bud development*.—Flower buds are borne in clusters of 3 and singly per stem.

Flower bloom:

*Fragrance*.—Light spicy perfume.

*Duration*.—The blooms have a duration on the plant of approximately 10 to 14 days. Petals fall cleanly away from plant after flowers have fully matured.

*Size*.—Flower diameter is 100 mm when open. Flower depth is 30 mm.

*Flower shape*.—General shape is an open cup with petals that curve out from the center.

*Shape of flower, side view*.—The upper portion is flat. The lower portions is flat.

Petalage: Under normal conditions, flowers have 33 petals total, 5 to 7 of which are petaloids.

General tonality of flower: Open flowers are Yellow Group 12B. Tonality remains the same for at least 10 days.

Petal color:

*Upon opening, outer and inner petals*.—Upper surface: Yellow Group 12A with shades of Yellow Group 13A. Lower surface: Yellow Group 12B with shades of Yellow Group 12A.

*Basal zone*.—No distinctive coloration at the petal base observed.

*After opening, outer and inner petals*.—Upper surface: Yellow Group 12B. Lower surface: Yellow Group 12A.

*Basal zone*.—No distinctive coloration at the petal base observed.

Petals:

*Petal reflex*.—Weak to none.

*Margin*.—Entire and uniform. Weak undulations of margin observed.

*Shape*.—Generally broadly elliptic. Apex shape: Rounded, occasionally cuspidate. Base shape: Acute.

*Size*.—45 mm (l)×45 mm (w).

*Texture*.—Smooth.

*Thickness*.—Average.

Petaloids:

*Size*.—25 mm (l) by 18 mm (w).

*Quantity*.—5-7.

*Shape*.—Irregular, asymmetric. Apex is rounded with a cleft. Base is acute.

*Color*.—Upper surface Yellow Group 12B. Lower surface Yellow Group 12A.

Reproductive organs:

*Pollen*.—None observed.

*Anthers*.—Size: 2 mm in length. Color: Greyed-Orange Group 163B. Quantity: 65 on average.

*Filaments*.—Color: Yellow Group 3B. Length: 10 mm.

*Pistils*.—Length: 8 mm. Quantity: 50 on average.

*Stigmas*.—Color: Yellow Group 8B.

*Styles*.—Color: Orange-Red Group 35A.

*Location of stigmas*.—Level in location relative to the length of the filaments and the height of the anthers.

*Hips*.—None Observed.

PLANT

Plant growth: Upright, bushy. Plants are 100 cm in height, and 75 cm wide.

Stems:

*Color*.—Juvenile growth: Yellow-Green Group 144A. Mature growth: Yellow-Green Group 144A.

*Length*.—On average, canes are 60 cm from the base of the plant to the flowering portion.

*Diameter*.—6 mm.

*Internodes*.—On mature canes, there is an average distance of 30 mm between nodes.

*Surface texture*.—Young wood: Smooth. Older wood: Smooth.

Long prickles:

*Incidence*.—10 prickles per 10 cm of stem.

*Size*.—Average length of prickles on mature stems is 13 mm.

*Shape*.—Upper portion is linear. Lower portion is concave.

*Color*.—Juvenile prickles: Yellow-Green Group 144B. Mature prickles: Greyed-Red Group 173A.

Plant foliage:

*Compound leaf*.—110 mm (l)×80 (w).

*Quantity*.—2 leaves per 10 cm of stem on average.

*Leaf bearing angle to the stem*.—60 degrees.

*Color of juvenile foliage*.—Upper side: Yellow-Green Group 144A. Lower side: Yellow-Green Group 144A. Anthocyanin: Greyed-Orange Group 175B at the margins.

*Color of mature foliage*.—Upper side: Yellow-Green Group 147A. Lower side: Yellow-Green Group 146B.

Plant leaves and leaflets:

*Stipules*.—Size: 20 mm in length. Quantity: 2 per compound leaf. Shape: Linear, slightly broad based with outward extending apecies. Margins: Finely serrated with few stipitate glands. Color: Yellow-Green Group 144A.

*Petiole*.—Length: 25 mm. Diameter: 2 mm.

*Upper surface*.—Color: Yellow-Green Group 144A.

*Lower surface*.—Color: Yellow-Green Group 144B.

*Rachis*.—Length: 40 mm. Upper surface: Yellow-Green Group 144A. Lower surface: Yellow-Green Group 144B. Color:

*Leaflet*.—Quantity: Normal number of leaflets leaves in middle of the stem is 5 leaflets. Margins: Serrated. Size: Average size of the terminal leaflet on normal leaves is 50 mm in length by 36 mm wide. Shape: Ovate. Base: Rounded. Apex: Cuspidate. Texture: Smooth. Thickness: Average. Arrangement: Odd pinnate. Venation: Reticulate. Glossiness: Very glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Floribunda rose class named 'Poulnap003', substantially as illustrated and described herein, due to its abundant (color) flowers, disease resistance, and extended period of bloom.

* * * * *